(12) United States Patent
Bond et al.

(10) Patent No.: US 12,204,548 B2
(45) Date of Patent: Jan. 21, 2025

(54) USER COHORT QUERY ENGINE

(71) Applicant: CEDARON MEDICAL, INC., Davis, CA (US)

(72) Inventors: Malcolm L Bond, Winters, CA (US); Nicholas D. Pearson, Sacramento, CA (US); Daniel Mayorga, West Sacramento, CA (US)

(73) Assignee: Cedaron Medical, Inc., Davis, CA (US)

( * ) Notice: Subject to any disclaimer, the term of this patent is extended or adjusted under 35 U.S.C. 154(b) by 122 days.

(21) Appl. No.: 18/075,145

(22) Filed: Dec. 5, 2022

(65) Prior Publication Data
US 2024/0184786 A1   Jun. 6, 2024

(51) Int. Cl.
  *G06F 16/2457*    (2019.01)
  *G06F 16/248*     (2019.01)
  *G16H 10/60*      (2018.01)

(52) U.S. Cl.
  CPC ...... *G06F 16/24573* (2019.01); *G06F 16/248* (2019.01); *G16H 10/60* (2018.01)

(58) Field of Classification Search
  CPC .. G06F 16/24573; G06F 16/248; G16H 10/60
  USPC ........................................................ 707/713
  See application file for complete search history.

(56) References Cited

U.S. PATENT DOCUMENTS

| 11,830,587 B2 * | 11/2023 | Lefkofsky ........... G06F 18/2115 |
| 2014/0052462 A1 * | 2/2014 | Bond ..................... G16H 15/00 705/2 |
| 2020/0211716 A1 * | 7/2020 | Lefkofsky ............ G06F 18/214 |
| 2022/0059240 A1 * | 2/2022 | Schaeffer ............... G16H 50/70 |

* cited by examiner

*Primary Examiner* — Michael Pham
(74) *Attorney, Agent, or Firm* — Kilpatrick Townsend & Stockton LLP

(57) ABSTRACT

Described herein is a cohort engine that generates a cohort of patients with respect to a selected key patient record. The cohort engine receives, via a first user interface (UI), a key patient record. A patient-cohort generator is launched to determine an initial set of patient records that are to be included in the patient cohort. A second UI is configured to provide the initial set of patient records, where the second UI comprises at least three panes. Upon receiving, via the second UI, an input corresponding to at least one identifier being modified, an equation (i.e., query) is generated based on a combination of identifiers included in the second pane. An updated set of patient records is provided in a third pane of the second UI in response to the at least one identifier being modified.

18 Claims, 11 Drawing Sheets

FIG. 5A

CardiacCare™ | Search Patients | Go | +New Patient | Harvest/Export ▾ Utilities ▾ Settings ▾ ⊙ Maintenance

Patient Search

Showing Search Results *(Show Recent)* — 1 Result(s) of 1 Patients

Search By

| | Last Name | First Name | Middle Name | MRN | Gender | DOB | Alternate ID |
|---|---|---|---|---|---|---|---|
| Patient Name ▾ | Smith | John | | 123456789 | | 10/26/1967 | |

John Smith ✕

Patient Type: All Patients ▾

Data Form: All Data Forms ▾

Facility: All Facilities ▾

[Clear] [Search]

| Data Form Name | Procedure Date | Facility Name | Account Number | Arrival Date | Admission Date | Discharge Date |
|---|---|---|---|---|---|---|
| ACC/NCDR CathPCI v5.0 | 10/9/2021 | Cedaron | | | 10/9/2021 | 10/13/2021 |
| STS Adult Cardiac Surgery v2.9 | 4/14/2021 | Cedaron | | 4/14/2021 | 4/14/2021 | 4/19/2021 |

500, 510, 515

ACC/NCDR CATHPCI v5.0

PATIENT
NAME: SMITH, JOHN (123456789)
DOB: 10/26/1967
VISIT DATE: 10/9/2021

SECTIONS
Z. ADMINISTRATION
A. DEMOGRAPHICS
B. EPISODE OF CARE
C. HISTORY AND RISK FACTORS
D. PRE-PROCEDURE INFORMATION
SAQ AND ROSE DYSPNEA SCALE
E. PROCEDURE INFORMATION
F. LABS

| | |
|---|---|
| ⊙ Peripheral Arterial Disease [4610:PriorPAD] | ○(Unspecified) ⊙No ○Yes |
| ⊙ Chronic Lung Disease [4576: HxChronicLung Diesease] | ○(Unspecified) ⊙No ○Yes |
| ⊙ Prior Coronary Artery Bypass Graft [4515: PriorCABAG] | ○(Unspecified) ⊙No ○Yes |
| ⊙ Tobacco Use [4625: TobaccoUse] | Former |
| ⊙ Cardiac Arrest Out Of Healthcare Facility [4630: CAOutHospital] | ○(Unspecified) ⊙No ○Yes |
| ⊙ Cardiac Arrest At Transferring Healthcare Facility [4635:CATransferFAC] (Known or Diagnosed Prior to First Cath Lab Visit) | |
| ⊙ Diabetes Mellitus [4555: Diabetes] | ○(Unspecified) ○No ⊙Yes |
| ⊙ Currently on Dialysis [4560: CurrentDialysis] | ○(Unspecified) ⊙No ○Yes |
| ⊙ Canadian Study of Health and Aging (CSHA) Clinical Frailty Scale [4561: CSHAScale] | 4: Vulnerable |

USER COHORT QUERY ENGINE

FIELD

The present disclosure relates generally to an improved data processing system and in particular to a health-related system technology for generating and reporting a user cohort via configurable user interfaces.

BACKGROUND

Computer and communication technologies continue to advance at a rapid pace. Indeed, computer and communication technologies are involved in many aspects of a user. Computers commonly include everything from hand-held computing devices to large multi-processor computer systems. Computer technology is becoming increasingly important in the medical services environment. For example, computers may assist health care providers in treating patients. In addition, computer systems may be used in the medical environment to assist clinicians and other health care providers.

With the ever-increasing number of patients in the healthcare industry, information technology systems utilized in medical organizations have provisioned for the creation and storage of medical records of the patients. In such systems, information pertaining to diagnostic information, medications prescribed, patient improvement (i.e., performance metrics), or the like can be obtained and processed in a seamless manner only with respect to a single patient in silo. However, the information technology systems lack the feature of generating a cohort of patients based on certain desirable and/or configurable criteria, and further utilizing information pertinent to the cohort across multiple patients in order to provide an improved healthcare experience. Embodiments discussed herein address these and other issues individually as well as collectively.

SUMMARY

The present disclosure relates generally to an improved data processing system and in particular to a health-related system technology for generating and reporting a user cohort via configurable user interfaces. Various embodiments are described herein, including methods, systems, non-transitory computer-readable storage media storing programs, code, or instructions executable by one or more processors, and the like. These illustrative embodiments are mentioned not to limit or define the disclosure, but to provide examples to aid understanding thereof. Additional embodiments are discussed in the detailed description section, and further description is provided therein.

An aspect of the present disclosure provides for a method for generating a patient cohort from a key patient record, the method comprising: receiving, via a first user interface (UI), a patient record selected from a plurality of patient records based on a selection criterion, wherein the patient record corresponds to the key patient record; responsive to receiving the key patient record, launching a patient-cohort generator to determine an initial set of patient records that are to be included in the patient cohort; configuring a second UI to provide the initial set of patient records, wherein the second UI comprises at least (1) a first pane including information associated with the key patient record, (2) a second pane including one or more identifiers and associated metadata, and (3) a third pane including the initial set of patient records, wherein each of the one or more identifiers included in the second pane comprises (i) an indicator having a value representative of an effect of the identifier with respect to a number of patient records to be included in the third pane, and (ii) an icon that enables removal of the identifier from the second pane; receiving, via the second UI, an input corresponding to at least one identifier being modified, wherein the receiving causes an equation based on a combination of identifiers included in the second pane to be generated; and obtaining, in response to the equation being generated, an updated set of patient records, the updated set of patient records being provided in the third pane of the second UI.

Another aspect of the present disclosure provides for a non-transitory computer readable medium storing specific computer-executable instructions that, when executed by a processor, cause a computer system to: receive, via a first user interface (UI), a patient record selected from a plurality of patient records based on a selection criterion, wherein the patient record corresponds to the key patient record; responsive to receiving the key patient record, launch a patient-cohort generator to determine an initial set of patient records that are to be included in the patient cohort; configure a second UI to provide the initial set of patient records, wherein the second UI comprises at least (1) a first pane including information associated with the key patient record, (2) a second pane including one or more identifiers and associated metadata, and (3) a third pane including the initial set of patient records, wherein each of the one or more identifiers included in the second pane comprises (i) an indicator having a value representative of an effect of the identifier with respect to a number of patient records to be included in the third pane, and (ii) an icon that enables removal of the identifier from the second pane; receive, via the second UI, an input corresponding to at least one identifier being modified, wherein the receiving causes an equation based on a combination of identifiers included in the second pane to be generated; and obtain, in response to the equation being generated, an updated set of patient records, the updated set of patient records being provided in the third pane of the second UI.

One aspect of the present disclosure provides for a computing device for generating a patient cohort from a key patient, the computing device comprising: a processor; and a memory including instructions that, when executed with the processor, cause the computing device to, at least: receive, via a first user interface (UI), a patient record selected from a plurality of patient records based on a selection criterion, wherein the patient record corresponds to the key patient record; responsive to receiving the key patient record, launch a patient-cohort generator to determine an initial set of patient records that are to be included in the patient cohort; configure a second UI to provide the initial set of patient records, wherein the second UI comprises at least (1) a first pane including information associated with the key patient record, (2) a second pane including one or more identifiers and associated metadata, and (3) a third pane including the initial set of patient records, wherein each of the one or more identifiers included in the second pane comprises (i) an indicator having a value representative of an effect of the identifier with respect to a number of patient records to be included in the third pane, and (ii) an icon that enables removal of the identifier from the second pane; receive, via the second UI, an input corresponding to at least one identifier being modified, wherein the receiving causes an equation based on a combination of identifiers included in the second pane to be generated; and obtain, in response to the equation being generated, an updated set of patient records, the updated set of patient records being provided in the third pane of the second UI.

The foregoing, together with other features and embodiments will become more apparent upon referring to the following specification, claims, and accompanying drawings.

BRIEF DESCRIPTION OF THE DRAWINGS

FIG. 5A depicts an exemplary first user interface (UI), in accordance with various embodiments.

FIG. 5C depicts an alternative first UI, in accordance with various embodiments.

FIG. 6A depicts an exemplary second UI, in accordance with various embodiments.

FIG. 6C depicts another exemplary portion of the second UI, in accordance with various embodiments.

DETAILED DESCRIPTION

In the following description, for the purposes of explanation, specific details are set forth in order to provide a thorough understanding of certain embodiments. However, it will be apparent that various embodiments may be practiced without these specific details. The figures and description are not intended to be restrictive. The word "exemplary" is used herein to mean "serving as an example, instance, or illustration." Any embodiment or design described herein as "exemplary" is not necessarily to be construed as preferred or advantageous over other embodiments or designs.

Figure 1:
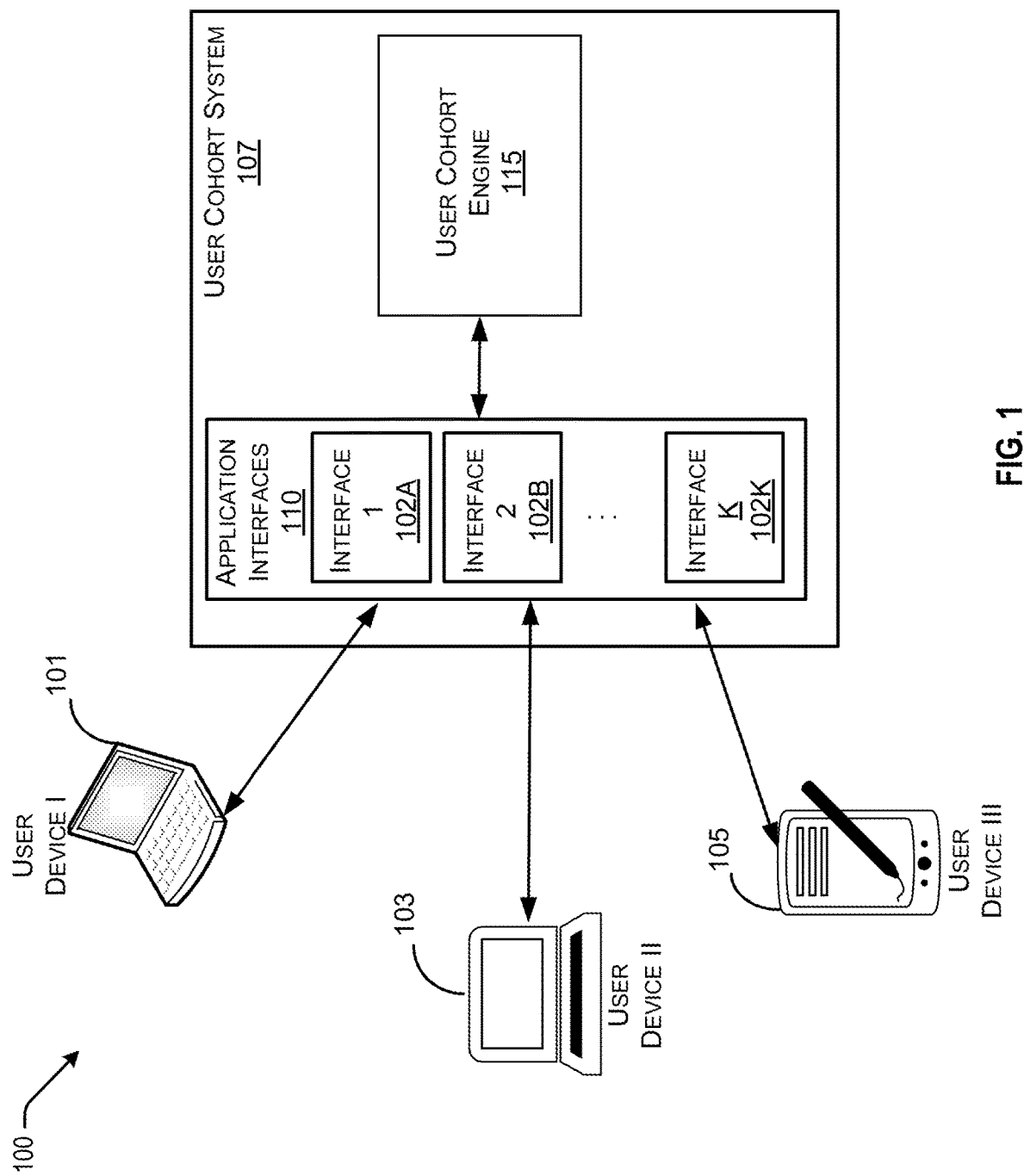
FIG. 1 depicts an exemplary high-level architecture of a user cohort system, in accordance with various embodiments.

FIG. 1 depicts an exemplary high-level architecture of a user cohort system, in accordance with various embodiments. The architecture 100 includes a plurality of communication devices e.g., user device I 101, user device II 103, and user device III 105 that are communicatively coupled to the user cohort system 107. The user devices may be a handheld portable device (e.g., an iPhone® cellular phone, an iPad® computing tablet, a PDA), a PC, a workstation, a mainframe, a kiosk, a server rack, or any other data processing device. The user devices may be communicatively coupled to the user cohort system 107 via a communication network e.g., a public network (such as the Internet) or may be alternatively hard wired connected to the user cohort system 107. Furthermore, the user devices may also communicatively couple with the user cohort system via Bluetooth, WiFi, or the like communication technologies.

The user cohort system 107 includes application interfaces 110 and a user cohort engine 115. The application interfaces 110 includes a set of one or more interfaces (e.g., graphical user interfaces (GUI) such as interface 1 (102A), interface 2 (102B) . . . interface K (102K). According to some embodiments, the set of one or more interfaces may correspond to a software platform(s) that allow users to interact with the user cohort engine 107. As will be described below, one or more of the interfaces is configurable based on certain user requirements. According to some embodiments, the user cohort engine 107 is configured to receive (e.g., from a first user interface) a request to generate or create a user cohort. The user cohort engine processes the user's request and provides (as response) the cohort of users (e.g., via a second configurable interface) in a seamless manner. An operator of a user device (e.g., user device I 101) may further utilize the provided cohort of users.

According to some embodiments, the user cohort system 107 corresponds to a cohort system configured to generate a cohort of users e.g., patients in a medical facility or organization. In such a scenario, an operator of user device I 101 may correspond to a medical professional such as a nurse, a doctor, or any other licensed medical professional. However, it is appreciated that in some cases, the operator of the user device I may also correspond to a patient that receives configured patient cohort information as described below. In what follows, there is provided a detailed architecture of the user cohort engine 115 along with a description of exemplary user interfaces utilized to provide (e.g., to an operator) the user cohort. It is appreciated that a cohort of users as defined herein corresponds to a group of users that share certain common characteristics. Furthermore, for sake of illustration, the description of the user cohort engine is provided with respect to users in a medical facility or organization (i.e., patients). Accordingly, the terms 'user cohort' and 'patient cohort' are used interchangeably and correspond to a group of users/patients that share certain common characteristics.

Figure 2:
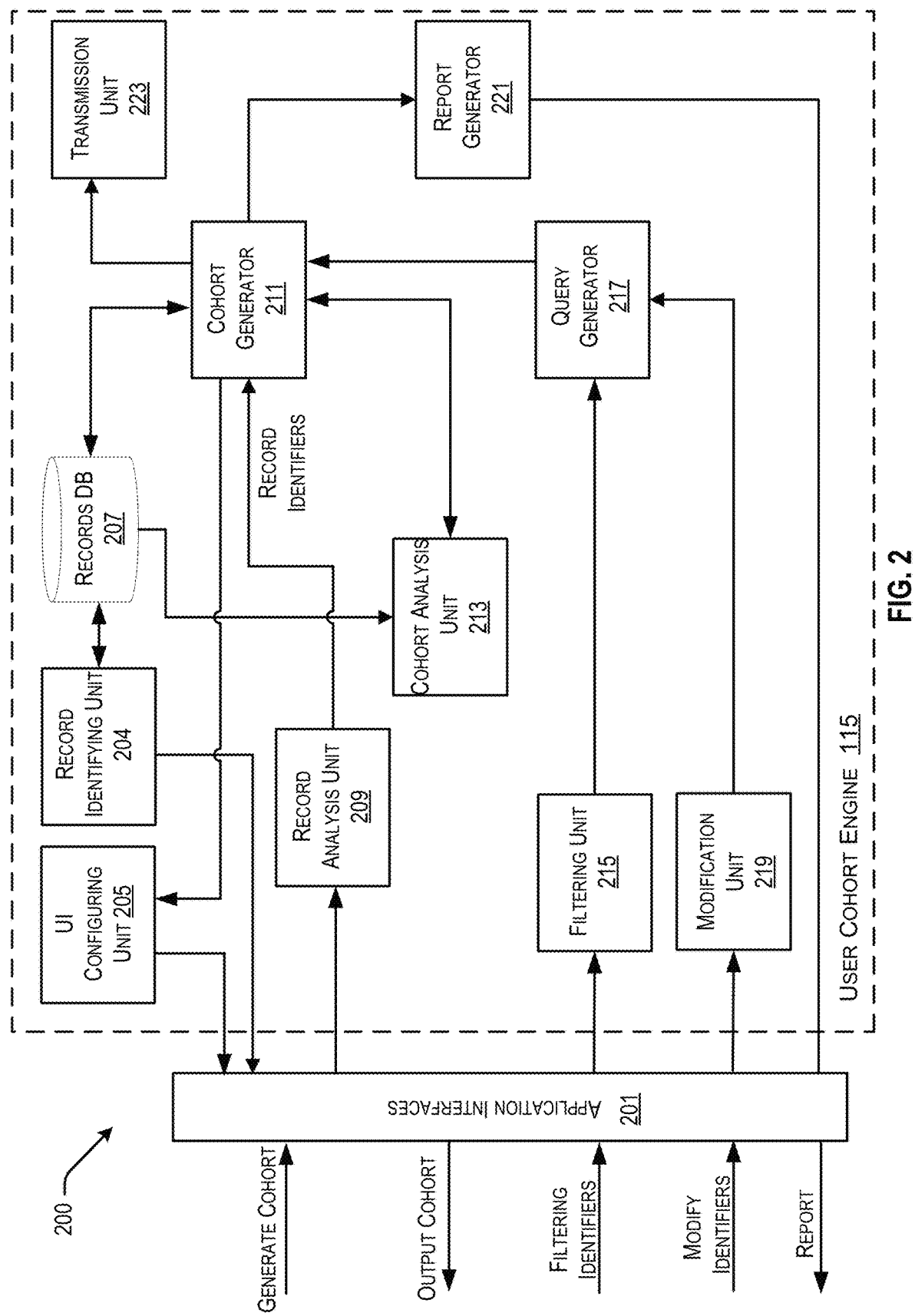
FIG. 2 depicts an exemplary detailed architecture of a user cohort engine included in the user cohort system, in accordance with various embodiments.

FIG. 2 depicts an exemplary detailed architecture of a user cohort engine included in the user cohort system, in accordance with various embodiments. According to some embodiments, the user cohort system 200 of the present disclosure includes a user cohort engine 115 and a plurality of application interfaces 201. The user cohort engine 115 communicates with external devices (e.g., user device I 101 of FIG. 1) via the plurality of application interfaces 201. The user cohort engine is configured to generate a user cohort (i.e., a set of patient records) based on a key patient record. In other words, the user cohort engine 115 identifies one or more patient records (included in the set of patient records), where each patient record is similar in some context to the key patient record i.e., the patient record shares some common characteristic(s) with respect to the key patient record. Details pertaining to the generation and presentation of the user cohort are described next.

The user cohort engine 115 includes a user interface (UI) configuring unit 205, a record identifying unit 204, a records database 207, a records analysis unit 209, a cohort generator 211, a cohort analysis unit 213, a filtering unit 215, a query generator 217, a modification unit 219, a report generator 221, and a transmission unit 223. According to some embodiments, the UI configuring unit 205 configures a first UI included in the application interfaces 201. An exemplary first UI is depicted in FIG. 5A. As shown in FIG. 5A, the first UI 500 includes a first pane 510 labeled as a 'patient search' pane. The first pane 510 provides for searching a particular patient record. As shown in FIG. 5A, a plurality of options are provided for searching the particular patient record. In one implementation, various search parameters are provided in the form of drop down menus in the first pane to enable searching for the particular patient record. For instance, the first pane 510 may include a first drop down menu to search by patient name, and other identifiers. Additionally, a second drop down menu may be provided to search for a type of patient, a third drop down menu to select particular data forms associated with the patient(s), as well as a fourth drop down menu may be provided to search patients with respect to facilities where the patient is treated.

Upon receiving respective inputs in the first pane 510 with regard to one or more search parameters, the record identifying unit 204 communicates with the records database 207 to retrieve a patient record corresponding to the search parameters. In one implementation, upon successfully identifying the patient record, the UI configuring unit 205 may provide the result (i.e., a patient record) and information associated with the patient record in a results display pane 515 of the first UI 500. For example, as shown in FIG. 5A, the search parameters include searching for a patient by name (i.e., John Smith). Accordingly, information associated with the patient record e.g., types of tests conducted (e.g., ACC/NCDR CATH PCI test, a cardiac surgery v 2.9 test, and the like), location of a stent being placed in the patient, etc., are provided in the results display pane 515 of the first UI 500.

Figure 5B:
FIG. 5B depicts another exemplary first UI, in accordance with various embodiments.

In some embodiments, upon receiving a selection (e.g., from a clinician) with respect to the information provided in the first UI 500, a modified view of the patient information is provided in the first UI. An exemplary modified view 550 is depicted in FIG. 5B, where the selection pertains to a particular test of the patient (i.e., ACC/NCDR CATH PCI test). The modified view 550 includes a first pane 518 that displays information (e.g., via drop down menus) related to the patient. The modified view 550 further includes a second pane 519 that displays information pertinent to the selected medical procedure associated with the patient i.e., information related to a medical test e.g., ACC/NCDR CATH PCI test. In some embodiments, there is provided in the second pane 519 of the first UI, an icon or a button 517 labeled as 'create patient cohort'. A selection of this icon or button (performed for example via a touch operation by the clinician) enables selection of the particular patient under consideration i.e., John Smith to be assigned as a key patient. Specifically, the user cohort engine 115 receives an indication that the patient record corresponding to John Smith is to be considered as the key patient record, with respect to which a user/patient cohort is to be generated.

FIG. 5C depicts an alternative view of the first UI, in accordance with various embodiments. Specifically, FIG. 5C depicts information provided in the first UI 555 upon selection of the particular test (i.e., ACC/NCDR CATH PCI test) associated with the key patient. As shown in FIG. 5C, in a first pane 531, there is provided detailed information related to the patient. The detailed information may be categorized under various categories such as administration, demographics, episodes of care, history and risk factors, and the like. Upon selection of a particular category e.g., history and risk factors, detailed information associated with the selected category is provided in a second pane 532. The detailed information associated with the selected category that is provided in the second pane 532 includes selectable parameters/identifiers associated with the patient record e.g., whether the patient is diabetic, whether the patient is on dialysis, whether the patient is a tobacco user, etc. It is appreciated that various parameters may be selected in order to generate the user cohort based on a set of desired parameters. Additionally, in the first UI 555 as depicted in FIG. 5C there is provided an icon/button 517 that provisions for selection of the patient record as corresponding to the key patient record with respect to which the user cohort is to be generated.

Figure 3:
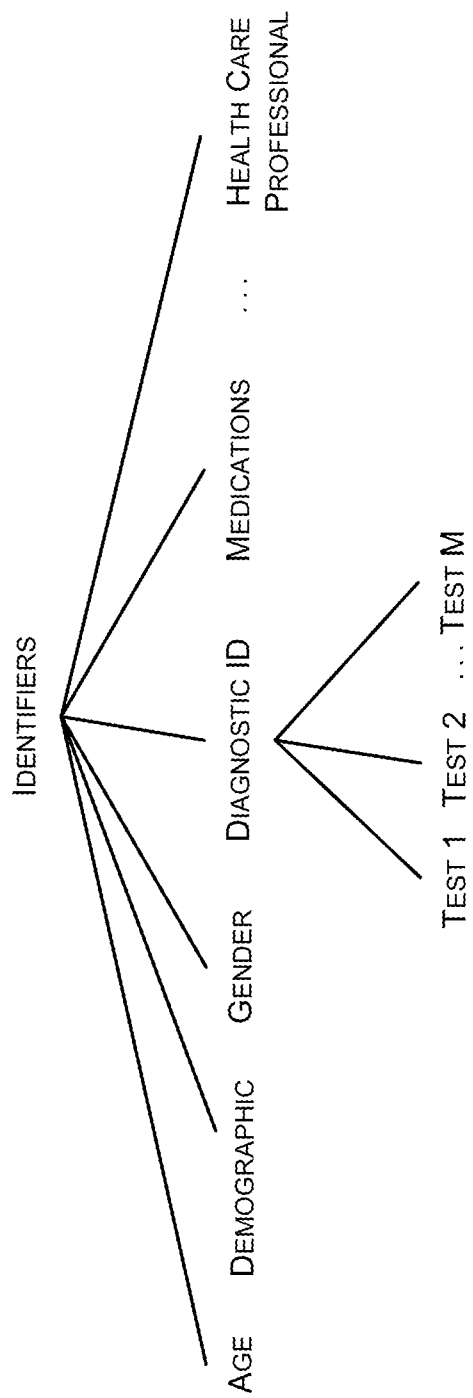
FIG. 3 depicts a tree graph illustrating different identifiers utilized in the user cohort system, in accordance with various embodiments.

It is noted that the above described embodiments of selecting the key patient record is in no way limiting the scope of the present disclosure. Additional modifications may be provided to the first UI, which are very well within the scope of the present disclosure. For example, the first UI may provide a personnel (e.g., clinician) a list of patient records. The clinician may select a particular patient record from the plurality of patient records to correspond to the key patient record (i.e., the record with respect to which the user/patient cohort is to be generated). The selection of the key patient record can be based on different conditions. For instance, according to some embodiments, each patient record is associated with a plurality of identifiers. FIG. 3 depicts exemplary identifiers that are associated with a patient record. As depicted in FIG. 3, the identifiers may include at least an age identifier, a demographic identifier, a diagnostic identifier (including one or more sub-identifiers associated with tests performed), a medical history identifier, a healthcare profession identifier and the like. One condition in selecting the key patient record may correspond to at least one of the one or more identifiers associated with the record satisfying a predetermined condition e.g., a value associated with the identifier (i.e., metadata of the identifier) being greater than/less than/or equal to a predetermined threshold value. Thus, in the embodiments as described above, an operator (e.g., a clinician) may issue a request to generate a user cohort by providing the user cohort engine 115 a selection of the key patient record.

Turning back to FIG. 2, the record analysis unit 209 receives as input the key patient record with respect to which the user cohort engine 115 generates the user cohort. The record analysis unit 209 extracts the one or more identifiers included in the key patient record. As stated previously with regard to FIG. 5C, it is noted that a subset of identifiers associated with the key patient record may be selected in order to generate the user cohort. Moreover, the identifiers included in the subset may be combined via Boolean operators (e.g., AND, OR, NOT, etc.) to form a logical string of identifiers i.e., a combination of identifiers formed via using one or more Boolean operators. Such a logical string of identifiers forms a filtering criterion to generate the user cohort. The identifiers associated with the key patient record are transmitted to the cohort generator 211.

The cohort generator 211 is configured to determine an initial set of patient records that are to be included in the patient cohort. The cohort generator 211 accesses the records database 207 to identify records that are to be included in the initial set of patient records. The cohort generator 211 determines whether a particular record is to be included in the initial set of patient records based on the particular record satisfying the filtering criterion. Upon determining the initial set of patient records, the cohort generator 211 triggers the UI configuring unit 205 to configure a second UI to provide the initial set of patient records.

Figure 6A:
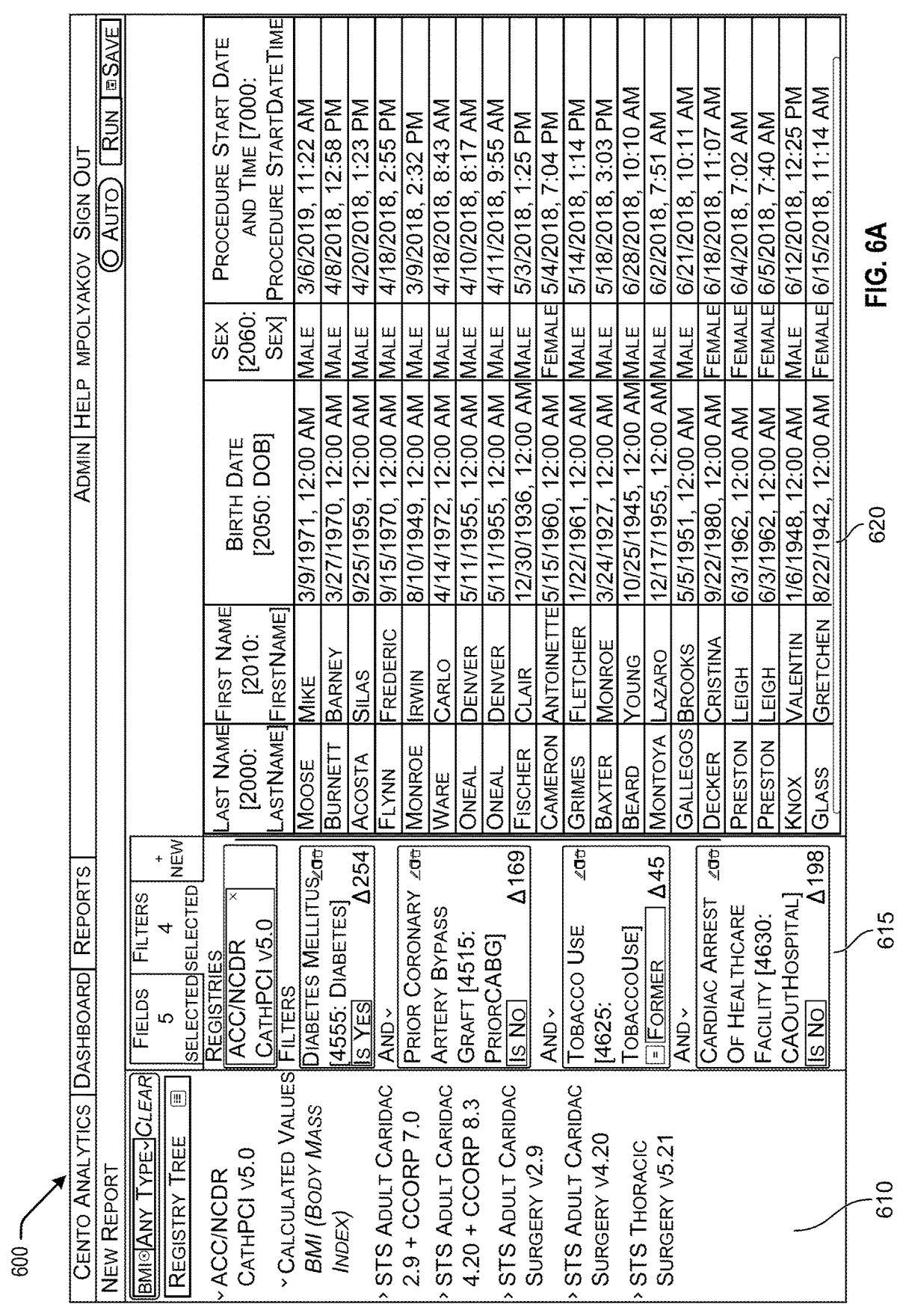

FIG. 6A depicts an exemplary second UI. According to some embodiments, the second UI 600 as depicted in FIG. 6A comprises at least three panes. A first pane 610 includes information associated with the key patient record. The information associated with the key patient record may correspond to a plurality of tests associated with the key patient record. A second pane 615 includes one or more identifiers of the key patient record that are used in the filtering criterion. For instance, referring to FIG. 6A, the second pane 615 depicts four identifiers (i.e., diabetes mellitus, prior coronary artery bypass, tobacco use, and cardiac arrest) that are used in the filtering criterion. It is appreciated that each identifier is associated with metadata that includes a value (e.g., numeric value, binary value, or the like) of the identifier. Moreover, as shown in FIG. 6A, the four identifiers are combined via logical operator (i.e., AND operator). It is appreciated that the identifiers included in the second pane 615 may be combined via any other logical operators e.g., OR operator. Further, the second UI 600 includes a third pane 620 that comprises the initial set of patient records.

Figure 6B:
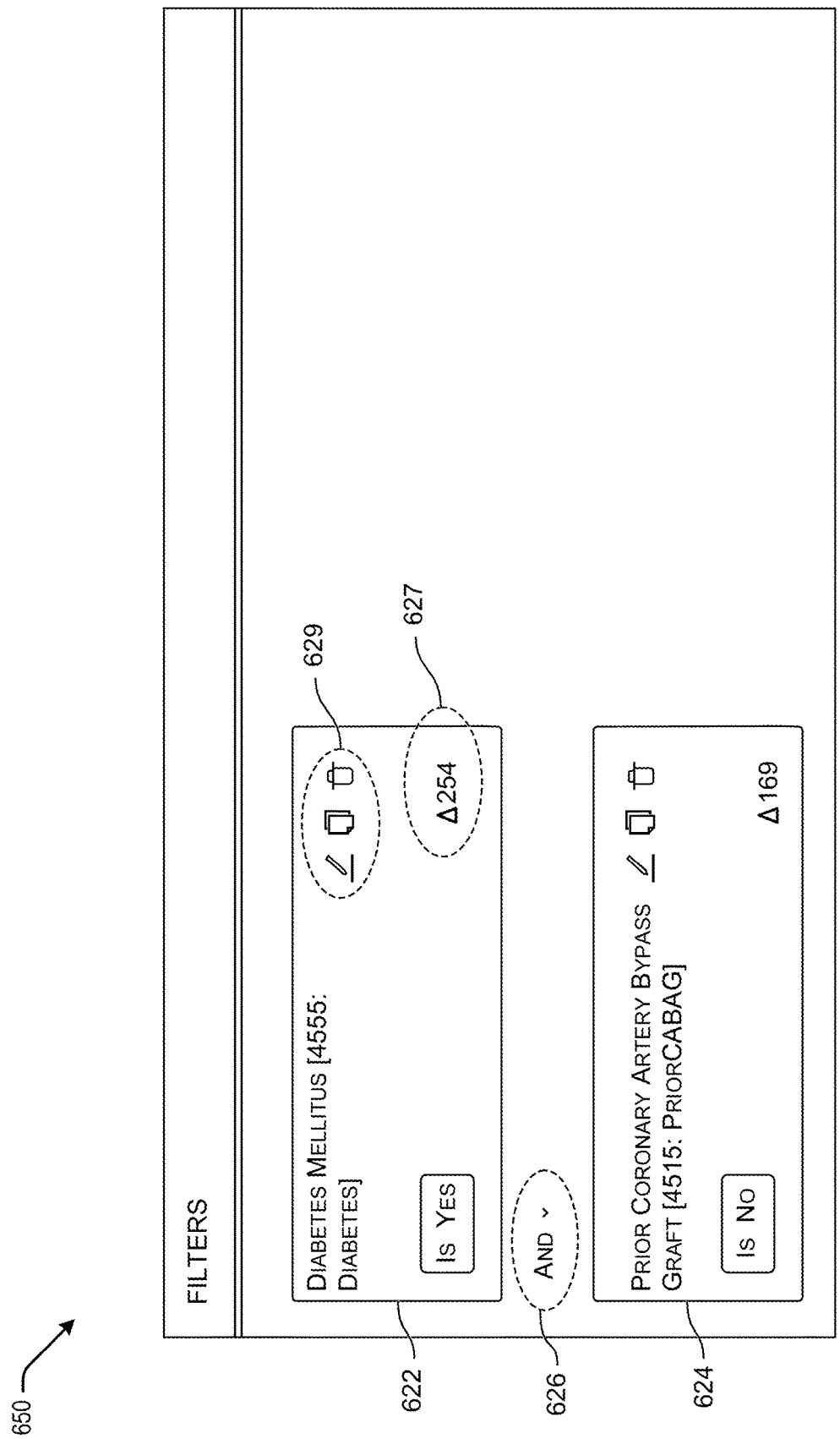
FIG. 6B depicts an exemplary portion of the second UI, in accordance with various embodiments.

According to some embodiments, the initial set of patient records and the one or more identifiers used in the filtering criterion are sent to the cohort analysis unit 213 for further processing. In one implementation, the cohort analysis unit 213 computes a value of an indicator that is to be associated with each identifier. FIG. 6B depicts exemplary identifiers that are used in the filtering criterion. For instance, FIG. 6B depicts two identifiers (i.e., diabetes mellitus 622 and prior coronary artery bypass graft 624) that are used in the filtering criterion. As shown in FIG. 6B, the identifier 622 is associated with an indicator 627 ('A' symbol) having a certain value. The value of the indicator represents an effect of the identifier with respect to a number of patient records to be included in the third pane of the second UI. For example, with reference to the identifier 622, the value of the indicator (i.e., 254) indicates that a total of 254 more records will be included in the initial set of records upon the identifier 622 being removed from the filtering criterion. By some embodiments, the cohort analysis unit 213 computes the value of the indicator as follows: (i) the cohort analysis unit obtains a first set of patient records by including the identifier in the filtering criterion and a second set of patient records by excluding the identifier from the filtering criterion, and (ii) computes the value representative of the effect of the identifier as a difference between a first number of patient records included in the first set of patient records and a second number of patient records included in the second set of patient records.

According to some embodiments, each identifier included in the second pane of the second UI includes a plurality of icons or buttons. For instance, as shown in FIG. 6B, the identifier 622 includes a plurality of icons 629. The plurality of icons or buttons may include a first icon corresponding to a 'delete icon'. Upon the contents of the second UI being presented to a user (e.g., a clinician), the delete icon provides a mechanism for the user to remove i.e., delete the corresponding identifier from being included in the filtering criterion. The plurality of icons or buttons 629 may further include a 'modify icon', which provides a mechanism to the user to modify metadata associated with the identifier. Details pertaining to the modification of an identifier are described next with reference to FIG. 6C.

Additionally, the plurality of icons or buttons 629 includes a 'de-clutter' icon or button. Such an icon is representative of the identifier being uncommon (i.e., rare). According to some embodiments, the cohort analysis unit 213 determines that a particular identifier is uncommon or unusual based on the identifier being an extremely limiting filter i.e., results in very few patient records being included in the third pane of the second UI. In one implementation, the de-clutter icon may be represented in the second UI using some visual display effects e.g., highlighting the icon, incorporating a blinking effect in the icon, etc. In doing so, the user (i.e., clinician) upon viewing such an icon may desire to remove the identifier from the filtering criterion or toggle the de-clutter button (e.g., in an OFF position) in order not to limit the number of records included in the third pane of the second UI.

Turning back to FIG. 2, the user cohort engine 115 provides, via the second UI, the initial set of patient records (in the third pane) to the user according to the above described embodiments. According to some embodiments, upon viewing the initial set of patient records in the second UI, the user may perform one or more operations e.g., filtering operation, modification operation, etc. It is noted that such operations may be performed by the user via a touch operation with respect to content included in the second UI. For instance, the user may desire to modify metadata associated with an identifier. An exemplary embodiment of modifying metadata associated with an identifier is depicted in FIG. 6C.

Figure 6C:
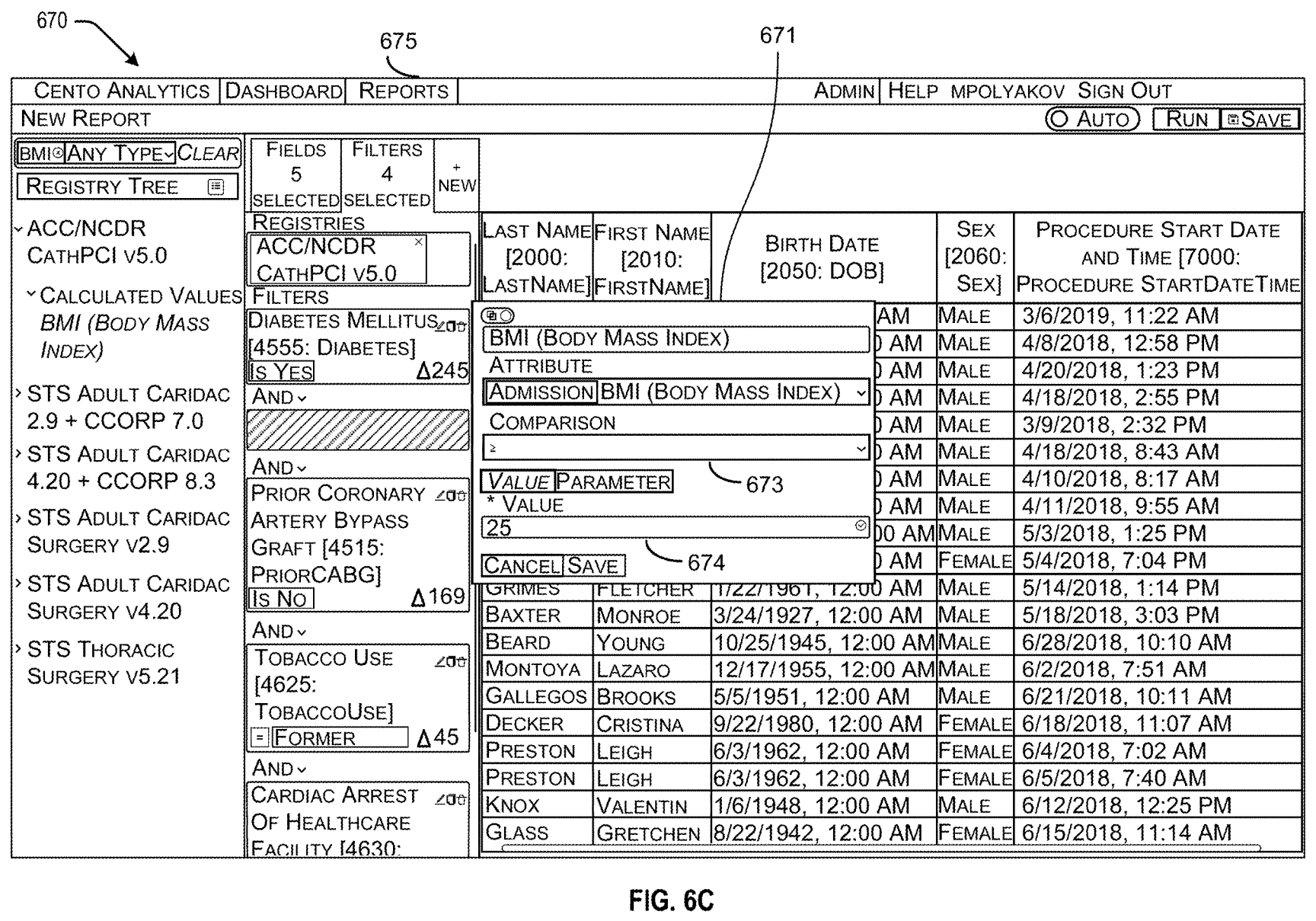

FIG. 6C depicts an example wherein the user selects the identifier e.g., body mass index (BMI) identifier for modification purposes. The modifications to the identifier can be executed in several ways. For instance, in one implementation, upon selecting the BMI identifier for modification, a pop-up window 671 associated with the BMI identifier may be presented to the user. It is noted that the BMI identifier may be selected for modification purposes by selecting the modify icon or button that is associated with the identifier (e.g., the modify icon included in the plurality of icons 629 of FIG. 6B). As shown in FIG. 6C, the pop-up window 671 includes information relevant to the selected identifier. For example, the pop-up window 671 includes a name of the identifier, a comparison operator 673 that is currently selected for the identifier, a value of the identifier 674, and the like. In one type of modification, the user may update the comparison operation e.g., change the comparison operator from an initial setting (e.g., greater than setting) to another setting (e.g., less than setting, or an equal to setting, etc.). It is appreciated that the user may select an option i.e., a relational operator to assign to the comparison operator via a drop down menu included in the pop-up window 671. Additionally, the user may desire to modify the value of the parameter 674 directly by inputting a new value for the BMI identifier.

Upon the user confirming the modifications performed with respect to the identifier (e.g., by clicking a save button in the pop-up window 671), an input indicating the modification of at least one identifier is received by the modification unit 219 of the user cohort engine 115. The modification unit 219 processes the modified identifier in addition to the other identifiers included in the filtering criterion and triggers the query generator 217. The query generator 217 is configured to issue a new query (e.g., SQL query) to the cohort generator 211 with respect to the newly modified filtering criterion. In response to receiving the query from the query generator 217, the cohort generator 211 accesses the records database 207 to obtain an updated set of patient records (i.e., records which satisfy the new filtering criterion) that are to be included in the third pane of the second UI and presented to the user.

In a manner similar to that as described above with respect to modifying an identifier, the user may also modify a number of identifiers included in the filtering criterion i.e., increase or decrease the number of identifiers used in the filtering criterion. For example, referring to FIG. 6A, the user may select one or more additional tests associated with the key patient record (i.e., from the first pane 610), and select one or more identifiers associated with the additional tests to be included in the filtering criterion. Similarly, referring to FIG. 6A, the user may delete an identifier from being included in the filtering criterion via utilizing the 'delete' icon associated with the identifier. Such modifications to the filtering criterion that are performed by the user causes the filtering unit 215 of the user cohort engine 115 to receive another input indicating the modifications. The filtering unit 215 triggers the query generator 217 to generate a query with respect to the modified filtering criterion. In turn, the query generator 217 triggers the cohort generator 211 to obtain an updated set of patient records (to be included in the third pane of the second UI) with respect to the modified filtering criterion.

According to some embodiments, the user cohort engine 115 is configured to generate and provide a report to the user (e.g., clinician). In one implementation, the user may click a report button or icon included in the second UI (e.g., button 657 as shown in FIG. 6C). In doing so, a request to generate a report is received by the user cohort engine 115. In turn the cohort generator 211 included in the user cohort engine 115 triggers the report generator 221 to configure a report of a format as desired by the user and provide the report via one of the application interfaces 201 to the user. In some embodiments, the user cohort engine 115 utilizes the transmission unit 223 to transmit an electronic message to a communication device of the user e.g., mobile device, computer, etc. The electronic message includes a web link that provides access to the updated set of patient records e.g., the user can view and download a report.

According to some embodiments, a customer of the user cohort system 107 of FIG. 1 may correspond to a patient e.g., the key patient. In such a case, the patient may utilize the user cohort system to identify other patients in the system that have similar medical diagnosis/tests as the key patient. In one implementation, upon receiving a request from the key patient to generate the user cohort, the user cohort system 107 may identify, a first patient record associated with a first patient based on a condition. For example, the user cohort system 107 may identify the first patient record that has a maximum level of similarity (e.g., with respect to the identifiers, tests conducted, etc.) with respect to the key patient record. Upon identifying the first patient record, the user cohort engine 115 may transmit an electronic message to a first mobile device operated by the first patient and a second mobile device operated by the key patient. In one implementation, the electronic message may be configured with a web-link, which upon activation (by both the first patient and the second patient) causes a communication channel between the first mobile device and the second mobile device to be setup. In this manner, the key patient can communicate with the first patient and receive (upon authorization of the first patient) information related to for example, treatments prescribed to the first patient, an improvement in health performance of the patient, etc., and utilize such information for comparison purposes and further evaluations.

Figure 4:
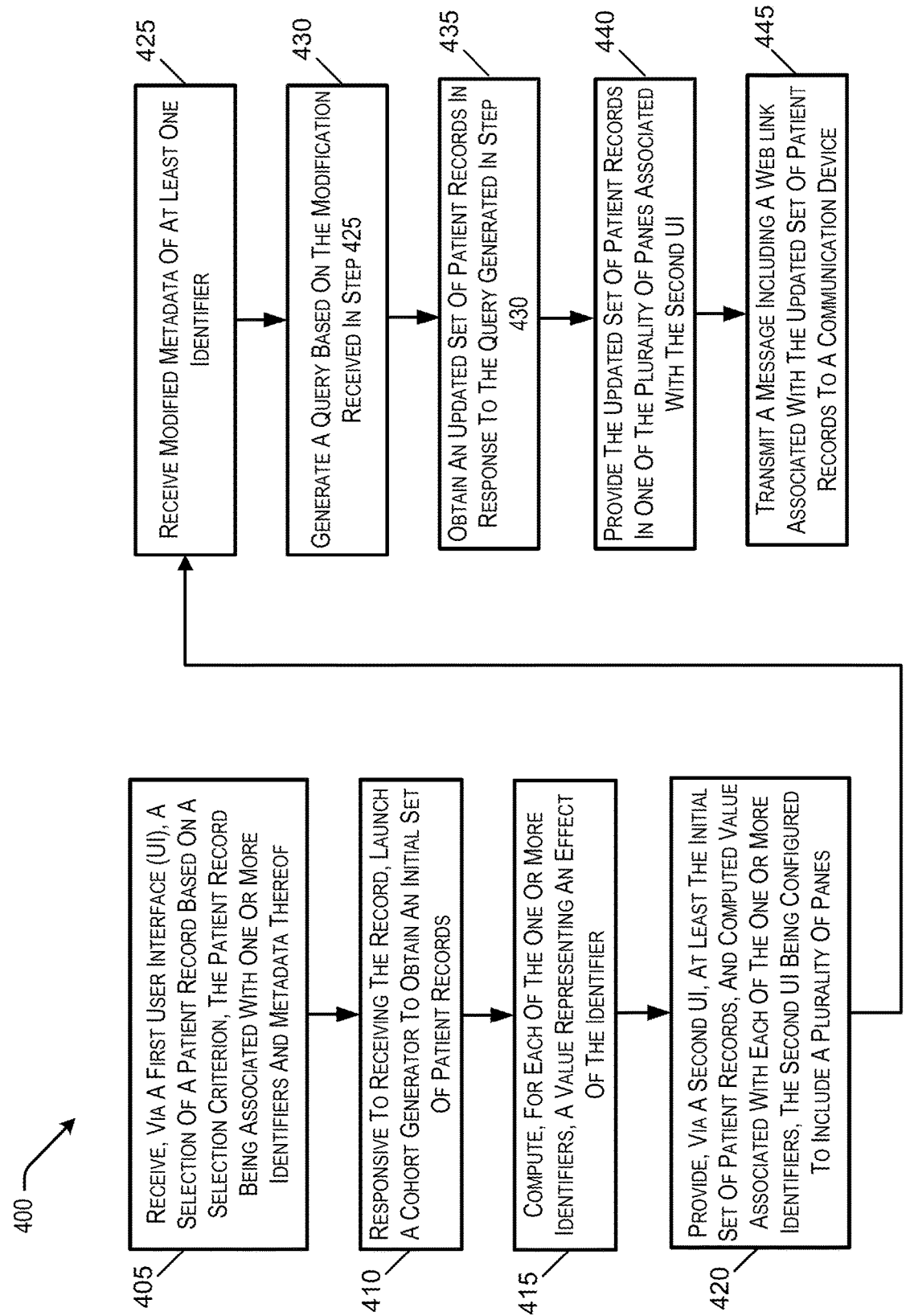
FIG. 4 depicts an exemplary flow diagram illustrating a process performed by the user cohort engine, in accordance with various embodiments.

FIG. 4 depicts an exemplary flow diagram illustrating a process performed by the user cohort engine, in accordance with various embodiments. The processing depicted in FIG. 4 may be implemented in software (e.g., code, instructions, program) executed by one or more processing units (e.g., processors, cores) of the respective systems, hardware, or combinations thereof. The software may be stored on a non-transitory storage medium (e.g., on a memory device). The method presented in FIG. 4 and described below is intended to be illustrative and non-limiting. Although FIG. 4 depicts the various processing steps occurring in a particular sequence or order, this is not intended to be limiting.

In certain alternative embodiments, the steps may be performed in some different order or some steps may also be performed in parallel.

The process commences in step 405, where a patient record is selected from a plurality of patient records based on a selection criterion. According to some embodiments, the selected patient record corresponds to a key patient. The user cohort (i.e., patient cohort) is generated with respect to the key patient. In one implementation, the user cohort engine receives a selection of one of the patient records (i.e., a record corresponding to the key patient). It is noted that each patient record is associated with one or more identifiers, where each identifier is associated with some metadata. The selection of the key patient record can be made based on a selection criterion that may correspond to, for instance, at least one of the one or more identifiers satisfying a predetermined condition. For instance, one of the identifiers may be a medical/diagnostic identifier (e.g., body mass index (BMI)). In such a case, the selection criterion may correspond to the BMI being greater than a predetermined threshold value, or the BMI being equal to a certain desired value, etc. It is appreciated that the selection of the key patient record may be based on multiple identifiers, where each identifier satisfies a unique condition.

Upon receiving the selection of the key patient record, the user cohort engine extracts the one or more identifiers associated with the selected record. It is noted that metadata associated with each of the one or more identifiers forms a filtering criterion to obtain an initial set of patient records that are to be included in the patient cohort. Specifically, in step 410, the user cohort engine launches a cohort generator to obtain the initial set of patient records to be included in the patient cohort. In one implementation, the cohort generator accesses a records database to identify records to be included in the initial set of patient records. In one implementation, the cohort generator determines whether a particular record is to be included in the initial set of patient records based on at least one identifier of the particular record satisfying one or more filtering criterion.

The process then moves to step 415, wherein for each of the one or more identifiers associated with the selected patient record, a value representing an effect of the identifier is computed. The value corresponds to an increase in a number of patient records to be included in the initial set of patient records responsive to the identifier being removed as a filtering criterion. In one implementation, the value of an identifier is computed as follows: obtain a first set (A) of patient records without using the identifier as a filtering criterion, and further obtain a second set (B) of patient records including the identifier as a filtering criterion. The value of the identifier is computed as a difference between a number of records included in set A and a number of records included in set B. In step 420, at least the initial set of patient records, the one or more identifiers associated with the key patient record, and the computed values (of step 415) for each of the one or more identifiers are provided via a second UI. It is noted that the cohort engine configures the second UI to include at least three panes, where a first pane includes information (e.g., medical tests and contextual information thereof) associated with the key patient record, a second pane includes one or more identifiers and associated metadata, and a third pane includes the set of patient records (e.g., patient cohort). It is appreciated that the second pane further includes the icons or buttons associated with each of the one or more identifiers as described previously with reference to FIG. 2.

The process then moves to step 425, where the user cohort engine receives an input indicative of metadata associated with at least one identifier being modified. In response to receiving the modified metadata, the user cohort engine generates a query to obtain an updated set of patient records (step 430). In one implementation, in response to receiving the modified metadata, the user cohort engine generates an equation based on a combination of identifiers included in the second pane. Such a combination of identifiers may be achieved via the usage of binary operators e.g., AND operator, OR operator etc.

The process then moves to step 435, where the user cohort engine obtains an updated set of patient records with respect to the query (e.g., the equation) generated in step 430. In step 440, the user cohort engine incorporates the updated set of patient records (obtained in step 435 in the third pane of the second UI. Further, in step 445, the user cohort engine proceeds to transmit an electronic message to a communication device (e.g., mobile device operated by the key patient and/or a communication device operated by a physician/clinician). In one implementation, the electronic message may include a web link associated with the updated set of patient records. As such, the physician, clinician, and/or the key patient may access the updated set of patient records by performing a touch operation on the provided web link.

Figure 7:
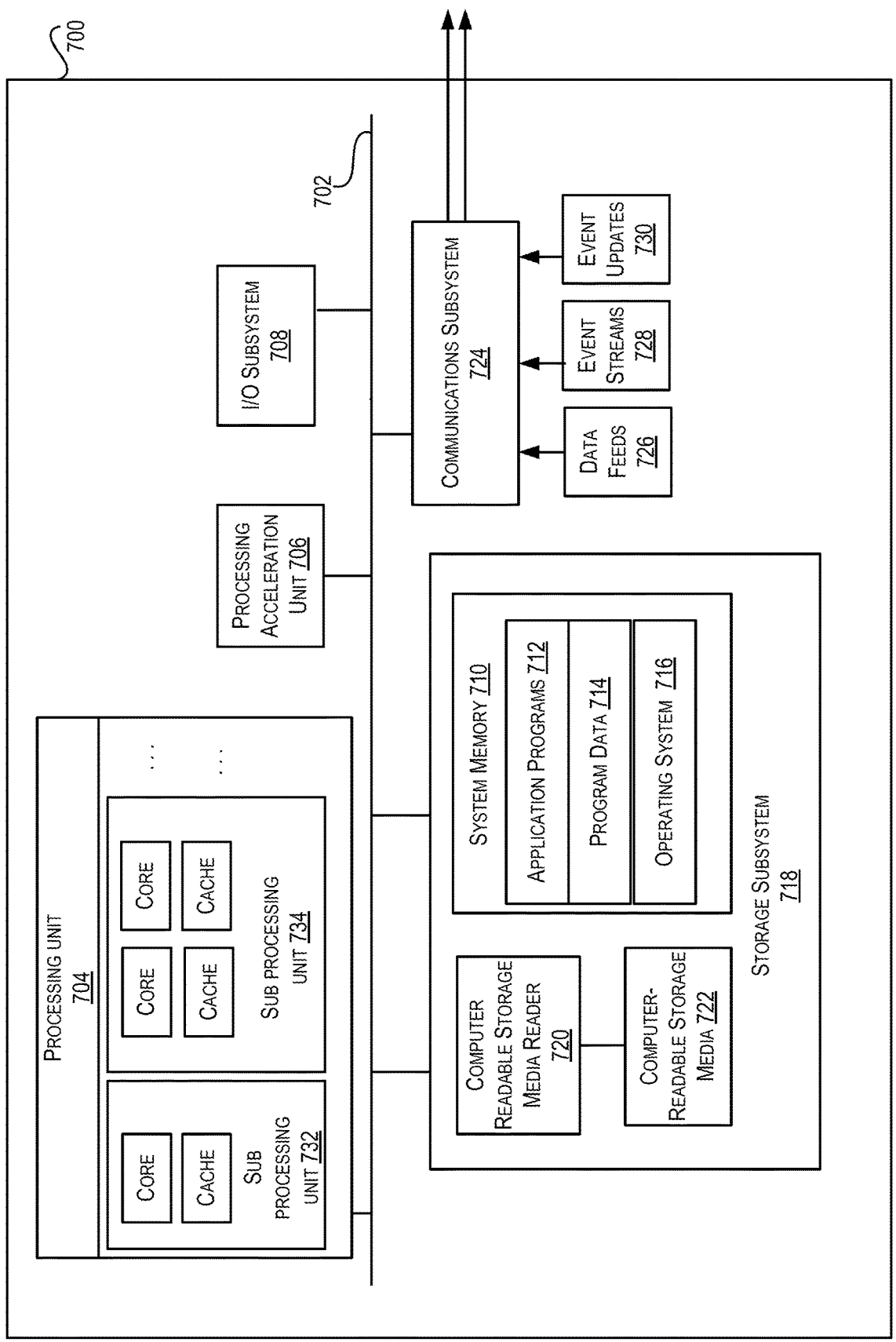
FIG. 7 is a block diagram illustrating an example computer system, according to at least one embodiment.

FIG. 7 illustrates an example computer system 700, in which various embodiments may be implemented. The system 700 may be used to implement any of the computer systems described above. As shown in the figure, computer system 700 includes a processing unit 704 that communicates with a number of peripheral subsystems via a bus subsystem 702. These peripheral subsystems may include a processing acceleration unit 706, an I/O subsystem 708, a storage subsystem 718 and a communications subsystem 724. Storage subsystem 718 includes tangible computer-readable storage media 722 and a system memory 710.

Bus subsystem 702 provides a mechanism for letting the various components and subsystems of computer system 700 communicate with each other as intended. Although bus subsystem 702 is shown schematically as a single bus, alternative embodiments of the bus subsystem may utilize multiple buses. Bus subsystem 702 may be any of several types of bus structures including a memory bus or memory controller, a peripheral bus, and a local bus using any of a variety of bus architectures. For example, such architectures may include an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard.

Processing unit 704, which can be implemented as one or more integrated circuits (e.g., a conventional microprocessor or microcontroller), controls the operation of computer system 700. One or more processors may be included in processing unit 704. These processors may include single core or multicore processors. In certain embodiments, processing unit 704 may be implemented as one or more independent processing units 732 and/or 734 with single or multicore processors included in each processing unit. In other embodiments, processing unit 704 may also be implemented as a quad-core processing unit formed by integrating two dual-core processors into a single chip.

In various embodiments, processing unit 704 can execute a variety of programs in response to program code and can maintain multiple concurrently executing programs or processes. At any given time, some or all of the program code to be executed can be resident in processor(s) 704 and/or in storage subsystem 718. Through suitable programming, processor(s) 704 can provide various functionalities described above. Computer system 700 may additionally include a processing acceleration unit 706, which can include a digital signal processor (DSP), a special-purpose processor, and/or the like.

I/O subsystem 708 may include user interface input devices and user interface output devices. User interface input devices may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. User interface input devices may include, for example, motion sensing and/or gesture recognition devices such as the Microsoft Kinect® motion sensor that enables users to control and interact with an input device, such as the Microsoft Xbox® 360 game controller, through a natural user interface using gestures and spoken commands. User interface input devices may also include eye gesture recognition devices such as the Google Glass® blink detector that detects eye activity (e.g., 'blinking' while taking pictures and/or making a menu selection) from users and transforms the eye gestures as input into an input device (e.g., Google Glass®). Additionally, user interface input devices may include voice recognition sensing devices that enable users to interact with voice recognition systems (e.g., Siri® navigator), through voice commands.

User interface input devices may also include, without limitation, three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additionally, user interface input devices may include, for example, medical imaging input devices such as computed tomography, magnetic resonance imaging, position emission tomography, medical ultrasonography devices. User interface input devices may also include, for example, audio input devices such as MIDI keyboards, digital musical instruments and the like.

User interface output devices may include a display subsystem, indicator lights, or non-visual displays such as audio output devices, etc. The display subsystem may be a cathode ray tube (CRT), a flat-panel device, such as that using a liquid crystal display (LCD) or plasma display, a projection device, a touch screen, and the like. In general, use of the term "output device" is intended to include all possible types of devices and mechanisms for outputting information from computer system 700 to a user or other computer. For example, user interface output devices may include, without limitation, a variety of display devices that visually convey text, graphics and audio/video information such as monitors, printers, speakers, headphones, automotive navigation systems, plotters, voice output devices, and modems.

Computer system 700 may comprise a storage subsystem 718 that comprises software elements, shown as being currently located within a system memory 710. System memory 710 may store program instructions that are loadable and executable on processing unit 704, as well as data generated during the execution of these programs.

Depending on the configuration and type of computer system 700, system memory 710 may be volatile (such as random access memory (RAM)) and/or non-volatile (such as read-only memory (ROM), flash memory, etc.) The RAM typically contains data and/or program modules that are immediately accessible to and/or presently being operated and executed by processing unit 704. In some implementations, system memory 710 may include multiple different types of memory, such as static random access memory (SRAM) or dynamic random access memory (DRAM). In some implementations, a basic input/output system (BIOS), containing the basic routines that help to transfer information between elements within computer system 700, such as during start-up, may typically be stored in the ROM. By way of example, and not limitation, system memory 710 also illustrates application programs 712, which may include client applications, Web browsers, mid-tier applications, relational database management systems (RDBMS), etc., program data 714, and an operating system 716. By way of example, operating system 716 may include various versions of Microsoft Windows®, Apple Macintosh®, and/or Linux operating systems, a variety of commercially-available UNIX® or UNIX-like operating systems (including without limitation the variety of GNU/Linux operating systems, the Google Chrome® OS, and the like) and/or mobile operating systems such as iOS, Windows® Phone, Android® OS, BlackBerry® 10 OS, and Palm® OS operating systems.

Storage subsystem 718 may also provide a tangible computer-readable storage medium for storing the basic programming and data constructs that provide the functionality of some embodiments. Software (programs, code modules, instructions) that when executed by a processor provide the functionality described above may be stored in storage subsystem 718. These software modules or instructions may be executed by processing unit 704. Storage subsystem 718 may also provide a repository for storing data used in accordance with the present disclosure.

Storage subsystem 700 may also include a computer-readable storage media reader 720 that can further be connected to computer-readable storage media 722. Together and, optionally, in combination with system memory 710, computer-readable storage media 722 may comprehensively represent remote, local, fixed, and/or removable storage devices plus storage media for temporarily and/or more permanently containing, storing, transmitting, and retrieving computer-readable information.

Computer-readable storage media 722 containing code, or portions of code, can also include any appropriate media known or used in the art, including storage media and communication media, such as but not limited to, volatile and non-volatile, removable and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. This can also include nontangible computer-readable media, such as data signals, data transmissions, or any other medium which can be used to transmit the desired information and which can be accessed by computing system 700.

By way of example, computer-readable storage media 722 may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray® disk, or other optical media. Computer-readable storage media 722 may include, but is not limited to, Zip® drives, flash memory cards, universal serial bus (USB) flash drives, secure digital (SD) cards, DVD disks, digital video tape, and the like. Computer-readable storage media 722 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 700.

Communications subsystem 724 provides an interface to other computer systems and networks. Communications subsystem 724 serves as an interface for receiving data from and transmitting data to other systems from computer system 700. For example, communications subsystem 724 may enable computer system 700 to connect to one or more devices via the Internet. In some embodiments communications subsystem 724 can include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.11 family standards, or other mobile communication technologies, or any combination thereof), global positioning system (GPS) receiver components, and/or other components. In some embodiments communications subsystem 724 can provide wired network connectivity (e.g., Ethernet) in addition to or instead of a wireless interface.

In some embodiments, communications subsystem 724 may also receive input communication in the form of structured and/or unstructured data feeds 726, event streams 728, event updates 730, and the like on behalf of one or more users who may use computer system 700.

By way of example, communications subsystem 724 may be configured to receive data feeds 726 in real-time from users of social networks and/or other communication services such as Twitter® feeds, Facebook® updates, web feeds such as Rich Site Summary (RSS) feeds, and/or real-time updates from one or more third party information sources.

Additionally, communications subsystem 724 may also be configured to receive data in the form of continuous data streams, which may include event streams 728 of real-time events and/or event updates 730, that may be continuous or unbounded in nature with no explicit end. Examples of applications that generate continuous data may include, for example, sensor data applications, financial tickers, network performance measuring tools (e.g. network monitoring and traffic management applications), clickstream analysis tools, automobile traffic monitoring, and the like.

Communications subsystem 724 may also be configured to output the structured and/or unstructured data feeds 726, event streams 728, event updates 730, and the like to one or more databases that may be in communication with one or more streaming data source computers coupled to computer system 700.

Computer system 700 can be one of various types, including a handheld portable device (e.g., an iPhone® cellular phone, an iPad® computing tablet, a PDA), a wearable device (e.g., a Google Glass® head mounted display), a PC, a workstation, a mainframe, a kiosk, a server rack, or any other data processing system.

Due to the ever-changing nature of computers and networks, the description of computer system 700 depicted in the figure is intended only as a specific example. Many other configurations having more or fewer components than the system depicted in the figure are possible. For example, customized hardware might also be used and/or particular elements might be implemented in hardware, firmware, software (including applets), or a combination. Further, connection to other computing devices, such as network input/output devices, may be employed. Based on the disclosure and teachings provided herein, a person of ordinary skill in the art will appreciate other ways and/or methods to implement the various embodiments.

Although specific embodiments have been described, various modifications, alterations, alternative constructions, and equivalents are also encompassed within the scope of the disclosure. Embodiments are not restricted to operation within certain specific data processing environments, but are free to operate within a plurality of data processing environments. Additionally, although embodiments have been described using a particular series of transactions and steps, it should be apparent to those skilled in the art that the scope of the present disclosure is not limited to the described series of transactions and steps. Various features and aspects of the above-described embodiments may be used individually or jointly.

Further, while embodiments have been described using a particular combination of hardware and software, it should be recognized that other combinations of hardware and software are also within the scope of the present disclosure. Embodiments may be implemented only in hardware, or only in software, or using combinations thereof. The various processes described herein can be implemented on the same processor or different processors in any combination. Accordingly, where components or modules are described as being configured to perform certain operations, such configuration can be accomplished, e.g., by designing electronic circuits to perform the operation, by programming programmable electronic circuits (such as microprocessors) to perform the operation, or any combination thereof. Processes can communicate using a variety of techniques including but not limited to conventional techniques for inter process communication, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific disclosure embodiments have been described, these are not intended to be limiting. Various modifications and equivalents are within the scope of the following claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known for carrying out the disclosure. Variations of those preferred embodiments may become apparent to those of ordinary skill in the art upon reading the foregoing description. Those of ordinary skill should be able to employ such variations as appropriate and the disclosure may be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein.

All references, including publications, patent applications, and patents, cited herein are hereby incorporated by reference to the same extent as if each reference were individually and specifically indicated to be incorporated by reference and were set forth in its entirety herein.

In the foregoing specification, aspects of the disclosure are described with reference to specific embodiments thereof, but those skilled in the art will recognize that the disclosure is not limited thereto. Various features and aspects of the above-described disclosure may be used individually or jointly. Further, embodiments can be utilized in any number of environments and applications beyond those described herein without departing from the broader spirit and scope of the specification. The specification and drawings are, accordingly, to be regarded as illustrative rather than restrictive.

What is claimed is:

1. A method for generating a patient cohort from a key patient record, the method comprising:
    receiving, via a first user interface (UI), a patient record selected from a plurality of patient records based on a selection criterion, wherein the patient record corresponds to the key patient record;
    responsive to receiving the key patient record, launching a patient-cohort generator to determine an initial set of patient records that are to be included in the patient cohort;
    configuring a second UI to provide the initial set of patient records, wherein the second UI comprises at least (1) a first pane including information associated with the key patient record, (2) a second pane including one or more identifiers and associated metadata, and (3) a third pane including the initial set of patient records, wherein each of the one or more identifiers included in the second pane comprises (i) an indicator having a value representative of an effect of the identifier with respect to a number of patient records to be included in the third pane, and (ii) an icon that enables removal of the identifier from the second pane;

receiving, via the second UI, an input corresponding to at least one identifier being modified, wherein the receiving causes an equation based on a combination of identifiers included in the second pane to be generated, wherein configuring the second UI includes:

obtaining a first set of patient records by including a first identifier in the equation and a second set of patient records by excluding the first identifier in the equation; an computing the value representative of the effect of the first identifier as a difference between a first number of patient records included in the first set of patient records and a second number of patient records included in the second set of patient records, the effect corresponding to an increase in the number of patient records included in the initial set of patient records responsive to the first identifier being deleted from the second pane; and obtaining, in response to the equation being generated, an updated set of patient records, the updated set of patient records being provided in the third pane of the second UI.

2. The method of claim 1, further comprising:

extracting the one or more identifiers from the key patient record, wherein the one or more identifiers include at least an age identifier, a demographic identifier, a diagnostic identifier, or a medical history identifier.

3. The method of claim 1, wherein the selection criterion corresponds to at least one of the one or more identifiers associated with the key patient record satisfying a predetermined condition.

4. The method of claim 1, wherein the information associated with the key patient record corresponds to a plurality of tests associated with the key patient record, and metadata associated with an identifier corresponds to a numeric value of the identifier.

5. The method of claim 1, wherein the input corresponds to metadata of at least one identifier being modified by incorporating one or more relational operators with respect to metadata to obtain a range that is to be associated with the identifier.

6. The method of claim 1, wherein the input corresponds to at least one identifier being deleted via the icon or a button from the second pane.

7. The method of claim 1, wherein the equation is generated by combining the identifiers included in the second pane of the second UI, via one or more logical operators.

8. The method of claim 1, wherein at least one identifier of the one or more identifiers included in the second pane of the second UI comprises a de-clutter icon or a de-clutter button that is indicative of the at least one identifier being uncommon.

9. The method of claim 1, further comprising:

transmitting an electronic message to a communication device of a personnel, the electronic message including a web link that provides access to the updated set of patient records.

10. A computing device for generating a patient cohort from a key patient record, the computing device comprising:

a processor; and a memory including instructions that, when executed with the processor, cause the computing device to, at least:

receive, via a first user interface (UI), a patient record selected from a plurality of patient records based on a selection criterion, wherein the patient record corresponds to the key patient record;

responsive to receiving the key patient record, launch a patient-cohort generator to determine an initial set of patient records that are to be included in the patient cohort;

configure a second UI to provide the initial set of patient records, wherein the second UI comprises at least (1) a first pane including information associated with the key patient record, (2) a second pane including one or more identifiers and associated metadata, and (3) a third pane including the initial set of patient records, wherein each of the one or more identifiers included in the second pane comprises (i) an indicator having a value representative of an effect of the identifier with respect to a number of patient records to be included in the third pane, and (ii) an icon that enables removal of the identifier from the second pane;

receive, via the second UI, an input corresponding to at least one identifier being modified, wherein the receiving causes an equation based on a combination of identifiers included in the second pane to be generated, wherein the second UI configured to obtain a first set of patient records by including a first identifier in the equation and a second set of patient records by excluding the first identifier in the equation; and compute the value representative of the effect of the first identifier as a difference between a first number of patient records included in the first set of patient records and a second number of patient records included in the second set of patient records, the effect corresponding to an increase in the number of patient records included in the initial set of patient records responsive to the first identifier being deleted from the second pane; and obtain, in response to the equation being generated, an updated set of patient records, the updated set of patient records being provided in the third pane of the second UI.

11. The computing device of claim 10, further configured to:

extract the one or more identifiers from the key patient record, wherein the one or more identifiers include at least an age identifier, a demographic identifier, a diagnostic identifier, or a medical history identifier.

12. The computing device of claim 10, wherein the information associated with the key patient record corresponds to a plurality of tests associated with the key patient record, and metadata associated with an identifier corresponds to a numeric value of the identifier.

13. The computing device of claim 10, wherein the input corresponds to metadata of at least one identifier being modified by incorporating one or more relational operators with respect to metadata to obtain a range that is to be associated with the identifier.

14. The computing device of claim 10, wherein the input corresponds to at least one identifier being deleted via the icon or a button from the second pane.

15. The computing device of claim 10, wherein at least one identifier of the one or more identifiers included in the second pane of the second UI comprises a de-clutter icon or a de-clutter button that is indicative of the at least one identifier being uncommon.

16. A non-transitory computer readable medium storing specific computer-executable instructions that, when executed by a processor, cause a computer system to generate a patient cohort from a key patient record, the computer system configured to at least:
receive, via a first user interface (UI), a patient record selected from a plurality of patient records based on a selection criterion, wherein the patient record corresponds to the key patient record;
responsive to receiving the key patient record, launch a patient-cohort generator to determine an initial set of patient records that are to be included in the patient cohort;
configure a second UI to provide the initial set of patient records, wherein the second UI comprises at least (1) a first pane including information associated with the key patient record, (2) a second pane including one or more identifiers and associated metadata, and (3) a third pane including the initial set of patient records, wherein each of the one or more identifiers included in the second pane comprises (i) an indicator having a value representative of an effect of the identifier with respect to a number of patient records to be included in the third pane, and (ii) an icon that enables removal of the identifier from the second pane;
receive, via the second UI, an input corresponding to at least one identifier being modified, wherein the receiving causes an equation based on a combination of identifiers included in the second pane to be generated, wherein the second UI configured to
obtain a first set of patient records by including a first identifier in the equation and a second set of patient records by excluding the first identifier in the equation; and
compute the value representative of the effect of the first identifier as a difference between a first number of patient records included in the first set of patient records and a second number of patient records included in the second set of patient records, the effect corresponding to an increase in the number of patient records included in the initial set of patient records responsive to the first identifier being deleted from the second pane; and
obtain, in response to the equation being generated, an updated set of patient records, the updated set of patient records being provided in the third pane of the second UI.

17. The non-transitory computer readable medium storing specific computer-executable instructions of claim 16, wherein at least one identifier of the one or more identifiers included in the second pane of the second UI comprises a de-clutter icon or a de-clutter button that is indicative of a level of rarity of the at least one identifier.

18. The non-transitory computer readable medium storing specific computer-executable instructions of claim 16, wherein the computer system is further configured to:
identify, from the patient cohort, a first patient record associated with a first patient based on a condition;
transmit an electronic message to a first mobile device operated by the first patient and a second mobile device operated by a key patient, wherein the electronic message includes a web-link which upon activation causes a communication channel between the first mobile device and the second mobile device to be setup.

* * * * *